United States Patent [19]

Morgan et al.

[11] Patent Number: 6,133,009
[45] Date of Patent: Oct. 17, 2000

[54] **TYPE II RESTRICTION ENDONUCLEASE, HPYCH4V, OBTAINABLE FROM *HELICOBACTER PYLORI* CH4 AND A PROCESS FOR PRODUCING THE SAME**

[76] Inventors: Richard D. Morgan, 31 Donovan's Way, Middleton, Mass. 01949; Qing Xu, 2601 Hillsboro Rd., C-11, Nashville, Tenn. 37212

[21] Appl. No.: 09/404,670

[22] Filed: Sep. 23, 1999

[51] Int. Cl.[7] ............................. C12N 9/22; C12N 15/55
[52] U.S. Cl. ................... 435/199; 435/252.3; 435/320.1; 536/23.2
[58] Field of Search ................................ 435/199, 252.3, 435/320.1; 536/23.2

[56] References Cited

U.S. PATENT DOCUMENTS 5,200,333   4/1993   Wilson ................................. 435/172.3

OTHER PUBLICATIONS

Endow, et al., J. Mol. Biol. 112:521 (1977).
Waalwijk, et al., Nucleic Acids Res., 5:3231 (1978).
Gingeras, et al., Proc. Natl. Acad. Sci., 80:402 (1983).
Gingeras, et al., Nucleic Acids Res. 5:4105 (1978).
Sanger, et al., Proc. Natl. Acad. Sci., 74:5463 (1977).
Brown, et al., J. Mol. 140:143 (1980).
Deverenx, et al., Nucleic Acids Res. 12:387 (1984).
Atlschul, et al., J. Mol. Biol. 215:403 (1990).
Gish, et al., Nature Genet., 3:266 (1993).

*Primary Examiner*—Charles L. Patterson, Jr.
*Attorney, Agent, or Firm*—Gregory D. Williams

[57] ABSTRACT

In accordance with the present invention, there is provided a novel restriction endonuclease and its DNA obtainable from *Helicobacter pylori* CH4 (NEB#1236), hereinafter referred to as "HpyCH4V", which endonuclease:

(1) recognizes the nucleotide sequence 5'-TGCA-3' in a double-stranded DNA molecule as shown below,

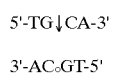

(wherein G represents guanine, C represents cytosine, A represents adenine, T represents thymine and N represents either G, C, A, or T);

(2) cleaves said sequence in the phosphodiester bonds between the G and C as indicated with the arrows; and (3) cleaves double-stranded pBR322 DNA to produce 21 fragments, including fragments of 576, 498, 441, 335, 315, 312, 296, 244 and 205 base pairs, and 12 fragments smaller than 200 base pairs.

9 Claims, 3 Drawing Sheets

```
    CGGAATGTTTTCCTACCCGCAAAAGAAATTGCGCAAGCTTTTTGAAGTCTTCCCTTTAGC
  1 ------------+----------+----------+----------+----------+----------+  60
              70         90        110
    CTTGATGGTTGAAAAAGCTAAAGGGGAAGCGTTTTATTTTGATAAGGGGGTGAAAAAGCG
 61 ------------+----------+----------+----------+----------+----------+ 120
             130        150        170
    TTTGCTAGAGCAAAGCGTAGAAAATTACCATGAAAAAAGCGAATGCTATTTAGCTAGCCA
121 ------------+----------+----------+----------+----------+----------+ 180
             190        210        230
    GCATGAAGCTCAAATTTTAGAAAAATATTTAAAGGGAAAATGATGCAAAATAGTGCTAAA
181 ------------+----------+----------+----------+----------+----------+ 240
             250        270        290
    AAATTAGAATATGAAGAGCGTTTTAATGACGCTCTTTTGAAATTAAAAGCATGCCAAGAA
241 ------------+----------+----------+----------+----------+----------+ 300
             310        330        350
    GAAAAACAAGTAGCAAGTTGTTTGAAATGCGAGAAGGTTTTAAAATGCGAGATTCGCAAC
301 ------------+----------+----------+----------+----------+----------+ 360
             370        390        410
    AACTATGTGGATGCGGCTTATGAAAGCATGAGTTTAGGCGAAGCGGGCGGGTTTGATTTC
361 ------------+----------+----------+----------+----------+----------+ 420
             430        450        470
    AACTAAAATGGGCTTAAAATGGTTAGTAACACTACCTTGCAAAAGAATTTAGACGCTTTT
421 ------------+----------+----------+----------+----------+----------+ 480
                      M  V  S  N  T  T  L  Q  K  N  L  D  A  F
             490        510        530
    TACACCCACCCCAAAATCGCACGATTTTGTTTGGATTTATTAAAAGATCTCATCCATCAA
481 ------------+----------+----------+----------+----------+----------+ 540
     Y  T  H  P  K  I  A  R  F  C  L  D  L  L  K  D  L  I  H  Q
             550        570        590
    AATCTAGGGCTAGACTTGAACGCGTTCCATTTTTTAGAGCCAAGTGCAGGGAGTGGGAGC
541 ------------+----------+----------+----------+----------+----------+ 600
     N  L  G  L  D  L  N  A  F  H  F  L  E  P  S  A  G  S  G  S
             610        630        650
    TTTGTTGGCGCGTTAAAAGGATTAGGGATTGCTGATTGTCTCGCCCTTGATATTGCCCCT
601 ------------+----------+----------+----------+----------+----------+ 660
     F  V  G  A  L  K  G  L  G  I  A  D  C  L  A  L  D  I  A  P
             670        690        710
    AAAGCTCAAGGCATTCAACAAAAAGATTATTTGTTGGAATTGATTGAGTTTAACAAAAAG
661 ------------+----------+----------+----------+----------+----------+ 720
     K  A  Q  G  I  Q  Q  K  D  Y  L  L  E  L  I  E  F  N  K  K
             730        750        770
    CGCATCATTATTGGCAACCCTCCTTTTGGACATAGGGGGAAACTGGCTCTAAATTTCTTA
721 ------------+----------+----------+----------+----------+----------+ 780
     R  I  I  I  G  N  P  P  F  G  H  R  G  K  L  A  L  N  F  L
             790        810        830
    AACAAATCTTTGAATGAAGCGCCTATTGTAGCGTTTATTTTGCCCAATTTATTCAAACGC
781 ------------+----------+----------+----------+----------+----------+ 840
     N  K  S  L  N  E  A  P  I  V  A  F  I  L  P  N  L  F  K  R
             850        870        890
    TATTCTATTCAAAAACACATTGATAAGCGTGCAAAATTGGTTTTAAACGCTGATTTAGAA
841 ------------+----------+----------+----------+----------+----------+ 900
     Y  S  I  Q  K  H  I  D  K  R  A  K  L  V  L  N  A  D  L  E
```

TYPE II RESTRICTION ENDONUCLEASE, HPYCH4V, OBTAINABLE FROM *HELICOBACTER PYLORI* CH4 AND A PROCESS FOR PRODUCING THE SAME

BACKGROUND OF THE INVENTION

The present invention relates to a new Type II restriction endonuclease, HpyCH4V, obtainable from *Helicobacter pylori* CH4, and to the process for producing the same.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. The majority of restriction endonucleases recognize sequences of 4 to 6 nucleotides in length, although recently a small number of restriction endonucleases which recognize 7 or 8 uniquely specified nucleotides have been isolated. Most recognition sequences contain a dyad axis of symmetry and in most cases all the nucleotides are uniquely specified. However, some restriction endonucleases have degenerate or relaxed specificities in that they recognize multiple bases at one or more positions in their recognition sequence, and some restriction endonucleases recognize asymmetric sequences. HaeIII, which recognizes the sequence 5'-GGCC-3', is an example of a restriction endonuclease having a symmetrical, non-degenerate recognition sequence, while HaeII, which recognizes 5'-(Pu)GCGC(Py)-3' typifies restriction endonucleases having a degenerate or relaxed recognition sequence. Endonucleases with symmetrical recognition sequences generally cleave symmetrically within or adjacent to the recognition site, while those that recognize asymmetric sequences tend to cleave at a distance of from 1 to 18 nucleotides away from the recognition site. More than two hundred unique restriction endonucleases have been identified among several thousands of bacterial species that have been examined to date.

Endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences 5'-(W)GGCC(W)-3' (SEQ ID NO:1), 5'-(Pu)GCGC(Py)-3' and 5'-GGCC-3' respectively. *Escherichia coli* RY13, on the other hand, synthesizes only one enzyme, EcoRI, which recognizes the sequence 5'-GAATTC-3' (SEQ ID NO:2).

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecule and cleaving them in each place that the recognition sequence occurs. The disintegration that results inactivates many of the infecting genes and renders the DNA susceptible to further degradation by exonucleases.

A second component of restriction systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always modified, by virtue of the activity of its modification methylase and it is therefore insensitive to the presence of the endogenous restriction endonuclease. It is only unmodified, and therefore identifiably foreign, DNA that is sensitive to restriction endonuclease recognition and attack. More than 3000 restriction endonucleases have been isolated from various bacterial strains. Of these, more than 200 recognize unique sequences, while the rest share common recognition specificities. Restriction endonucleases which recognize the same nucleotide sequence are termed "isoschizomers." Although the recognition sequences of isoschizomers are the same, they may vary with respect to site of cleavage (e.g., XmaI v. SmaI, Endow, et al., *J. Mol. Biol.* 112:521 (1977); Waalwijk, et al., *Nucleic Acids Res.* 5:3231 (1978)) and in cleavage rate at various sites (XhoI v. PaeR7I, Gingeras, et al., *Proc. Natl. Acad. Sci. U.S.A.* 80:402 (1983)).

There is a continuing need for novel Type II restriction endonucleases. Although Type II restriction endonucleases which recognize a number of specific nucleotide sequences are currently available, new restriction endonucleases which recognize novel sequences provide greater opportunities and ability for genetic manipulation. Each new unique endonuclease enables scientists to precisely cleave DNA at new positions within the DNA molecule, with all the opportunities this offers.

SUMMARY OF THE INVENTION

In accordance with the present invention, there is provided a novel restriction endonuclease obtainable from *Helicobacter pylori* CH4 (NEB#1236), hereinafter referred to as "HpyCH4V", which endonuclease:

(1) recognizes the nucleotide sequence 5'-TGCA-3' in a double-stranded DNA molecule as shown below,

5'-TG↓CA-3'

3'-AC↑GT-5'

(wherein G represents guanine, C represents cytosine, A represents adenine, T represents thymine and N represents either G, C, A, or T);

(2) cleaves said sequence in the phosphodiester bonds between the G and C as indicated with the arrows to create blunt ends; and (3) cleaves double-stranded pBR322 DNA to produce 21 fragments, including fragments of 576, 498, 441, 335, 315, 312, 296, 244 and 205 base pairs, and 12 fragments smaller than 200 base pairs.

The present invention further relates to a process for the production of the novel restriction endonuclease HpyCH4V. This process comprises either culturing *Helicobacter pylori* Ch4 under conditions suitable for expressing HpyCH4V, collecting the cultured cells, obtaining a cell-free extract therefrom and separating and collecting the restriction endonuclease HpyCH4V from the cell-free extract, or culturing a transformed host, such as *E. coli*, containing the genes for the HpyCH4V methylase and endonuclease, collecting the cultured cells, obtaining a cell-free extract therefrom and aseparating and collecting the restriction endonuclease HpyCH4V from the cell-free extract.

DETAILED DESCRIPTION OF THE INVENTION

Figure 1:
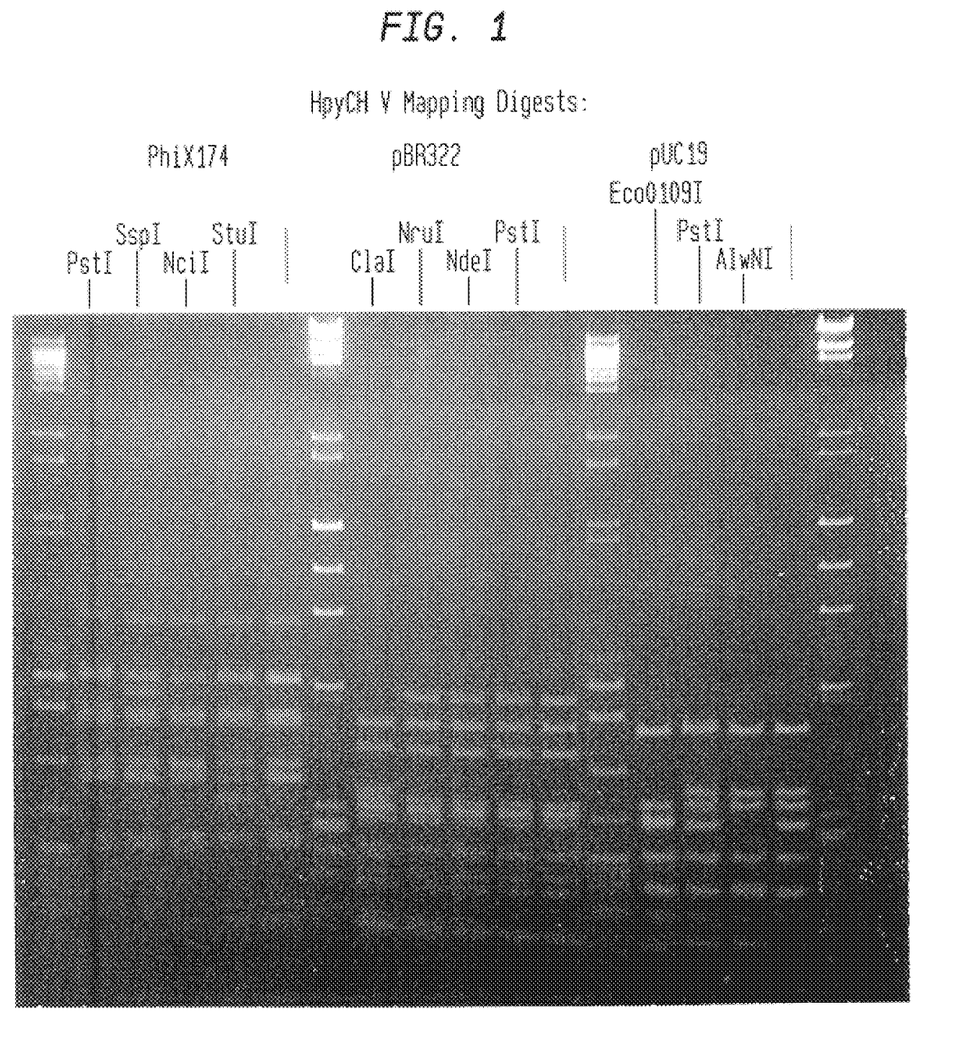
FIG. 1—Agarose gel showing HpyCH4V cleavage of various DNAs.

The recognition sequence of the endonuclease of the present invention may be determined by mapping the locations of several HpyCH4V cleavage sites in various DNAs and comparing the DNA sequences of these regions for homology, then comparing the predicted cleavage fragments of the putative recognition sequence with the observed restriction fragments produced by HpyCH4V cleavage of various DNAS. The endonuclease HpyCH4V was found to cleave pBR322 DNA more than ten times, producing fragments of approximately 575, 500, 450, 340, 320, 300, 250 and 200 bp, along with a number of smaller fragments. The location of several cut sites were mapped to approximate positions of 250 and 4040 (the 575 bp fragment) by simultaneously digesting PhiX174 DNA with HpyCH4V and with endonucleases which cleave at known positions, such as ClaI, NruI, NdeI, and PstI (FIG. 1). The approximate size of several of the DNA fragments produced by HpyCH4V digestion of pBR322 DNA was entered into the program SITES (Gingeras, et al., *Nucl. Acids Res.* 5:4105 (1978)), which generates potential recognition sequences for the input data by comparing the fragment sizes which would result from cleavage of the DNA at any given recognition pattern with the input fragment sizes. One such potential pattern generated was 5'-TGCA-3', which occurs in pBR322 DNA at positions consistent with the mapping data obtained, i.e. at positions 250 and 4037. The size of fragments predicted from cleavage at the sequence 5'-TGCA-3' in pBR322, pUC19 and PhiX174 DNAs matched the observed size of fragments from cleavage of these DNAs with HpyCH4V, from which we conclude that HpyCH4V recognizes the sequence 5'-TGCA-3'.

The point of cleavage within the HpyCH4V recognition sequence may be determined through dideoxy sequencing analysis of the terminal base sequence obtained from HpyCH4V cleavage of a suitable DNA substrate (Sanger, et al., *PNAS* 74:5463–5467 (1977) Brown, et al., *J. Mol. Biol.* 140:143–148 (1980)). By the above referenced method (FIG. 2, exemplified in Example II) it was found that HpyCH4V cleaves the phosphodiester bond between the G and the C in the recognition sequence 5'-TGCA-3' to produce a blunt end extension, as indicated by the arrows:

In accordance with the present invention, HpyCH4V is obtained by culturing *Helicobacter pylori* CH4 and recovering the endonuclease from the cells. A sample of *Helicobacter pylori* CH4 (NEB#1236) has been deposited under the terms and conditions of the Budapest Treaty with the American Type Culture Collection (ATCC) on Sep. 23, 1999 and bears the Patent Accession No. PTA-781.

For recovering the enzyme of the present invention *Helicobacter pylori* CH4 may be grown using any suitable technique. For example, *Helicobacter pylori* CH4 may be grown in Brucella broth media (BBL Microbiology Systems, Cockeysville, Md.) incubated at 37° C. Cells in the late logarithmic stage of growth are collected by centrifugation and either disrupted immediately or stored frozen at −70° C.

The HpyCH4V enzyme can be isolated from *Helicobacter pylori* CH4 cells by conventional protein purification techniques. For example, cell paste is suspended in a buffer solution and treated by sonication, high pressure dispersion or enzymatic digestion to allow extraction of the endonuclease by the buffer solution. Intact cells and cellular debris are then removed by centrifugation to produce a cell-free extract containing HpyCH4V. The HpyCH4V endonuclease is then purified from the cell-free extract by ion-exchange chromatography, affinity chromatography, molecular sieve chromatography, or a combination of these methods to produce the endonuclease of the present invention.

The endonuclease of the present invention along with its corresponding methylase may also be obtained using recombinant DNA techniques, such as the methylation selection technique disclosed by Wilson, et al., U.S. Pat. No. 5,200,333. As an example, DNA from a bacterial strain which contains an R-M system, such as *Helicobacter pylori*, is purified, partially digested with suitable type II endonucleases, and ligated to an appropriate cleaved, dephosphorylated cloning vector. The ligated DNA is transformed into an appropriate host, such as *E. coli*, the transformants are pooled and the population of cloning vectors are purified to form libraries. The library of clones is then challenged by digesting with an endonuclease which will selectively destroy vectors which do not contain and express the methylase of the R-M system being cloned. Vectors which contain and express the methylase gene of interest will be modified at the endonuclease recognition sites of the challenging endonuclease and thus be immune from cleavage. The challenged clone pools are then transformed back into the appropriate host to recover the undigested, presumably methylase expressing clones. The transformants may be screened for endonuclease activity or cycled through further rounds of purification and selection. Finally, individual transformants are selected and their DNA purified. These clones are analyzed for resistance to cleavage by the endonuclease of interest and for common insert DNA. Cell extracts prepared from transformants which demonstrate endonuclease resistance are assayed in vitro for methyltransferase and endonuclease activities.

The present invention is further illustrated by the following Examples. These Examples are provided to aid in the understanding of the invention and are not construed as a limitation thereof.

The references cited above and below are herein incorporated by reference.

EXAMPLE I

Production of HpyCH4V Endonuclease

*Helicobacter pylori* CH4 strain NEB#1236 was grown in Brucella broth media. The cells were incubated anaerobically under 5% $CO_2$ at 37° C. until late logarithmic stage. The cells were then harvested by centrifugation and stored frozen at −70° C.

8 grams of the cells obtained above were suspended in 40 mls buffer A (20 mM Tris-HCl, 0.1 mM EDTA, 1 mM dithiothreitol, 5% glycerol, pH 7.6 at 25° C.) adjusted to 50 mM NaCl. The cell suspension was sonicated until approximately 50 mg protein per gram of cells was released. The lysate was centrifuged at 15,000 rpm for 20 minutes at 4° C. in a Beckman JA17 rotor. 44 ml of supernatant was obtained containing approximately 400 mg of soluble protein.

The supernatant solution was applied to a 20 ml Heparin Hyper-D column (Biosepra, Marlborough, Mass.) equilibrated in buffer A adjusted to 50 mM NaCl. A 40 ml wash of buffer A adjusted to 50 mM NaCl was applied, then a 200 ml linear gradient of NaCl from 50 mM to 1M in buffer A was applied and fractions of 4 ml were collected. Fractions were assayed for HpyCH4V endonuclease activity by incubation with 1 µg Lambda DNA (NEB) in 50 µl NEBuffer 4 for one hour at 37° C. HpyCH4V activity eluted at 0.31M to 0.49M NaCl.

The Heparin Hyper-D column fractions containing the HpyCH4V activity were pooled, diluted to 100 mM NaCl in buffer A and applied to a 3 ml Heparin-TSK column (Toso-Haas, Philadelphia, Pa.), and a 50 ml linear gradient from 0.1M to 0.6M NaCl in buffer A was applied to the Heparin-TSK column. The HpyCH4V activity eluted between 0.2M to 0.4M NaCl. The Heparin-TSK fractions containing HpyCH4V activity were pooled, diluted to 50 mM NaCl in buffer A and applied to a 1 ml Mono-Q column (Pharmacia, Piscataway, N.J.), and a 50 ml linear gradient from 0.1 M to 0.6 M NaCl in buffer A was applied to the column. The HpyCH4V activity eluted between 0.12M to 0.15M NaCl and contained approximately 1000 units of HpyCH4V endonuclease activity. The HpyCH4V obtained was substantially pure and free of contaminating endonuclease and exonuclease activities. Bovine serum albumin was added as a stabilizer to a final concentration of 200 µg/ml and the HpyCH4V enzyme was dialyzed against storage buffer (50% glycerol, 50 mM NaCl, 20 mM Tris-HCl, 0.1 mM dithiothreitol, pH 7.5).

Activity determination

HpyCH4V activity: Samples of from 1 to 10 µl were added to 50 µl of substrate solution consisting of 1X NEBuffer 4 containing 1 µg Lambda phage DNA. The reaction was incubated at 37° C. for 5 to 60 mins. The reaction was terminated by adding 15 µls of a stop solution (50% glycerol, 50 mM EDTA pH 8.0, and 0.02% Bromophenol Blue). The reaction mixture was applied to a 1.2% agarose gel and electrophoresed. The bands obtained were identified in comparison with DNA size standards.

Unit Definition: One unit of HpyCH4V is defined as the amount of HpyCH4V required to completely cleave 1.0 µg of Lambda DNA in a total reaction volume of 50 µl NEBuffer 4, supplemented with 100 µg/ml bovine serum albumin, within one hour at 37° C.

EXAMPLE II

Determination of the HpyCH4V Cleavage Site

The location of HpyCH4V cleavage relative to the recognition sequence was determined by cleavage of a primer extension product, which was then electrophoresed alongside a set of standard dideoxy sequencing reactions produced from the same primer and template. M13mp18 DNA was employed as the template utilizing two HpyCH4V recognition sites at positions 6272 and 6280, which sites were conveniently located 30 and 38 bp 3' of a priming site for a standard sequencing primer: Sequenase –40 primer (5'-dGTTTTCCCAGTCACGAC-3' (SEQ ID NO:5)

Sequencing Reactions

The sequencing reactions were performed using the Sequenase version 2.0 DNA sequencing kit (Amersham Life Science) with modifications for the cleavage site determination. The template and primer were assembled in a 0.5 mL eppendorf tube by combining 2.5 µl dH2O, 3 µl 5X sequencing buffer (200 mM Tris pH 7.5, 250 mM NaCl, 100 mM MgCl2), 8 µl M13mp18 single-stranded DNA (1.6 µg) and 1.5 µl of primer (Sequenase –40 primer at 0.5 µM concentration). The primer-template solutions were incubated at 65° C. for 2 minutes, then cooled to 37° C. over 20 minutes in a beaker of 65° C. water on the benchtop to anneal the primer. The labeling mix (diluted 1:20) and sequenase were diluted according to manufacturer's instructions. The annealed primer and template tube was placed on ice. To this tube were added 1.5 µl 100 mM DTT, 3 µl diluted dGTP labeling mix, 1 µl [α-$^{33}$P] DATP (2000 Ci/mmole, 10 mCi/ml) and 3 µl diluted T7 Sequenase polymerase. The reaction was mixed and incubated at room temperature for 4 minutes. 3.5 µl of this reaction was then transferred into each of four tubes containing 2.5 µl termination mix for the A, C, G and T sequencing termination reactions. To the remaining reaction was added to 10 µl of Sequence Extending Mix, which is a mixture of dNTPs (no ddNTPs) to allow extension of the primer through and well beyond the HpyCH4V site with no terminations to create a labeled strand of DNA extending through the HpyCH4V recognition site for subsequent cleavage. The reactions were incubated 5 minutes at 37° C. To the A, C, G and T reactions were added 4 µl of stop solution and the samples were stored on ice. The extension reaction was then incubated at 70° C. for 20 minutes to inactivate the DNA polymerase (Sequenase), then cooled on ice. 10 µl of the extension reaction was then placed in one 0.5 ml eppendorf tube while 7 µl was placed in a second tube. To the first tube was added 1 µl (approximately 0.5 unit) HpyCH4V endonuclease, the reaction was mixed, and then 2 µl was transferred to the second tube. These enzyme digest reactions were mixed and then incubated at 37° C. for 1 hour, following which the reactions were divided in half. To one half 4 µl of stop solution was added and mixed (the minus polymerase reaction). To the second half was added 0.4 ul Klenow DNA polymerase (NEB#210) containing 80 µM dNTPs and the reactions were incubated at room temperature for 15 minutes, following which 4 µl of stop solution was added. The sequencing reaction products were electrophoresed on an 6% Bis-Acrylamide sequencing gel (Novex QuickPoint system), with the HpyCH4V digestions of the extension reaction next to the set of sequencing reactions produced from the same primer and template combination.

Figure 2:
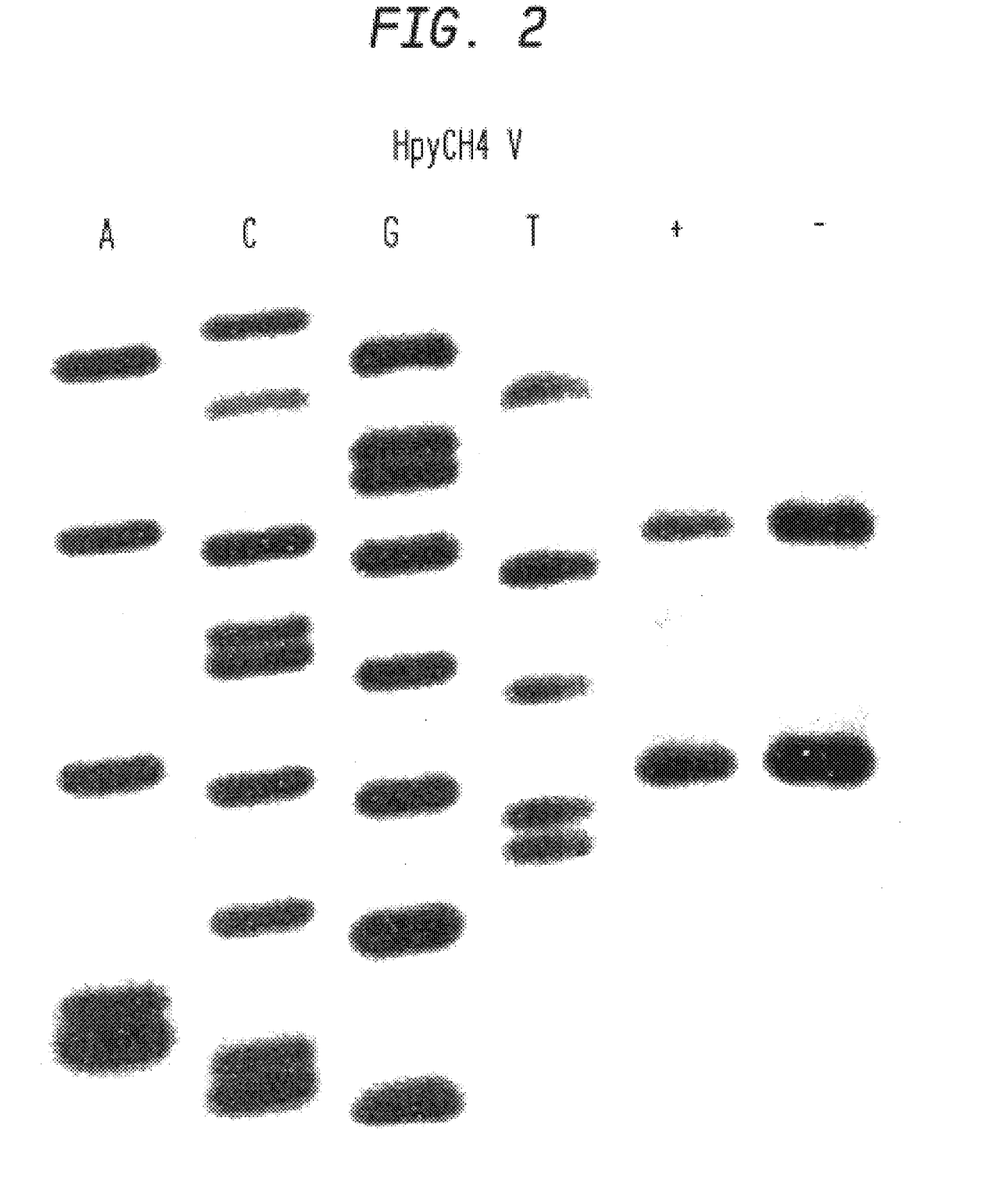
FIG. 2—Determination of the HpyCH4V cleavage site.

Results:

Digestion of the extension reaction product from the –40 primer with HpyCH4V endonuclease produced a band which co-migrated with the G nucleotide of the HpyCH4V recognition sequence 5'-TGCA-3', indicating cleavage between the G and the C of the recognition sequence. Treatment of the cleaved extension reaction product with Klenow DNA polymerase produced a band which also co-migrated with the G nucleotide of the HpyCH4V recognition sequence 5'-TGCA-3', indicating cleavage between the G and the C of the recognition sequence on the opposite strand of DNA as well (FIG. 2). These results indicate HpyCH4V cleaves DNA between the G and C in its recognition sequence on both DNA strands 5'-TG↓CA-3', to produce blunt-ended fragments.

EXAMPLE III

Cloning the HpyCH4V Endonuclease and Methylase

1. DNA purification: To prepare the genomic DNA of *Helicobacter pylori* CH4, 1 gram of cell paste was resuspended in 10 ml of 25% sucrose, 0.05 M Tris-HCl pH 8.0, to which was added 5 ml of 0.25 M EDTA, pH 8.0. Then 3 ml of lysozyme solution (10 mg/ml lysozyme in 0.25 M Tris-HCl, pH 8.0) was added and the cell suspension was incubated at 4° C. for 16 hours. 12 ml of Lytic mix (1% Triton-X100, 0.05 M Tris, 62 mM EDTA, pH 8.0) and 2.5 ml of 10% SDS was then added and the solution was incubated at 37° C. for 5 minutes. The solution was extracted with one volume of equilibrated phenol:chloroform:isoamyl alcohol (50:48:2, v/v/v) and the aqueous phase was recovered and extracted with one volume of chloroform:isoamyl alcohol (24:1, v/v) two times. The aqueous solution was then dialysed against four changes of 2 L of 10 mM Tris, 1 mM EDTA, pH 8.0. The dialysed DNA solution was digested with RNase (100 $\mu$g/ml) at 37° C. for 1 hour. The DNA was precipitated by the addition of 1/10th volume 5 M NaCl and 0.55 volumes of 2-propanol and spooled on a glass rod. The DNA was briefly rinsed in 70% ethanol, air dried and dissolved in 3 ml TE (10 mM Tris, 1 mM EDTA, pH 8.0) to a concentration of approximately 300 mg/ml and stored at 4° C.

2. Construction of libraries of genomic

*Helicobacter pylori* CH4 DNA in a selectable vector:

*Helicobacter pylori* CH4 genomic DNA was partially digested with either of two frequent cutting enzymes, Sau3AI or AciI. The partial digestion was carried out by serial dilution of the Sau3AI or the AciI restriction endonuclease from 0.5 units/$\mu$g DNA to 0.016 units/$\mu$g in the manufacturer's reaction buffer and digesting at 37° C. for 1 hour. The reactions were subsequently terminated by phenol:chloroform extraction. Reactions which produced an average size range of fragments from 2 to 6 kb were used for library construction. 3 $\mu$g of this partially digested HpyCH4V genomic DNA was ligated to 1 $\mu$g of the vector pUC19 (previously cleaved by BamHI (Sau3AI) or AccI (AciI) and dephosphorylated with calf intestinal alkaline phosphatase) in a final volume of 50 $\mu$l in 1X NEB ligase buffer with 1000 units (NEB) of T4 DNA ligase. The ligation reactions were incubated at 16° C. for 16 hours. 10 ul of each ligation reaction mixture was then transformed by electroporation into *E. coli* ER2683 cells and grown out in 10 ml L-Broth for 1 hour. 10 $\mu$l was then plated onto L-Broth agar plates supplemented with 100 $\mu$g/ml ampicillin to count the number transformants and the plates were incubated at 37° C. overnight. The remaining outgrowth was grown overnight in 250 ml L-Broth supplemented with 100 $\mu$g/ml ampicillin with shaking at 37° C. A total of 1×10$^6$ individual transformants were obtained for the Sau3Ai library, and 6×10$^5$ transformants for the AciI library. The cells of the 250 ml liquid culture were harvested by centrifugation at 5 K rpm for 5 minutes. The plasmids from these cells were purified by a standard alkaline lysis procedure, followed by four rounds of desalting in an Amicon Centricon-50 microconcentration device, washing with TE buffer each round, and then the plasmids were precipitated by PEG precipitation (combined 672 $\mu$l centricon purified plasmid, 128 $\mu$l 5 M NaCl and 800 $\mu$l 13% PEG-8000, incubated at 4° C. for 30 min, microfuged at 4° C. at maximum speed for 10 minutes, washed 2X with 70% cold ethanol) and resuspended in TE buffer at a concentration of 250 $\mu$g/ml.

3. HpyCH4V methylase selection: 1 $\mu$g of the plasmid library was digested for 2 hours at 37° C. in 50 $\mu$l 1X NEB#4 buffer with 4 units of the HpyCH4V prepared as above from *Helicobacter pylori* CH4 cells. 10 $\mu$l of the HpyCH4V digestion reaction was then transformed into 100 $\mu$l *E. coli* ER2683 competent cells and plated on L-broth plates containing 100 ug/ml ampicillin and the plates incubated at 37° C. overnight. In the initial attempt, a total of 3 transformants were obtained from the AciI library digested with 4 units from HpyCH4V and none from the Sau3AI library. The 3 AciI library clones were analyzed as follows: Plasmid from each colony was isolated by miniprep procedures and digested with HpyCH4V endonuclease.

Analysis of plasmid clones: Individual transformants were inoculated into 10 ml cultures of L-broth containing 100 $\mu$g/ml ampicillin and the plasmids that they carried were prepared by Qiagen QIAprep® Spin Miniprep columns according to the manufacturers instructions. Plasmids were assayed for the presence of the HpyCH4V methylase by digestion with HpyCH4V endonuclease.

All three of the clones analyzed from the AciI library were found to be fully protected from HpyCH4V digestion. All three clones were tested for the expression of HpyCH4V restriction activity when grown in L-Broth containing 100 $\mu$g/ml ampicillin. 1 of the 3 clones analyzed was found to express HpyCH4V restriction activity. This clone was designated pHpyCH4VA3 (strain NEB#1240) and may be used to produce HpyCH4V endonuclease by propagation to mid-log phase in a fermenter containing L-broth medium with ampicillin (100 $\mu$g/ml). The cells are harvested by centrifugation and may be stored at −20° C. or used immediately.

4. Purification of the HpyCH4V restriction endonuclease from NEB #1240 can be accomplished by a combination of standard protein purification techniques, such as affinity-chromatography or ion-exchange chromatography, as outlined above. The HpyCH4V restriction endonuclease obtained from this purification is substantially pure and free of non-specific endonuclease and exonuclease contamination.

EXAMPLE IV

Sequencing the HpyCH4V Endonuclease and Methylase

Figure 3:
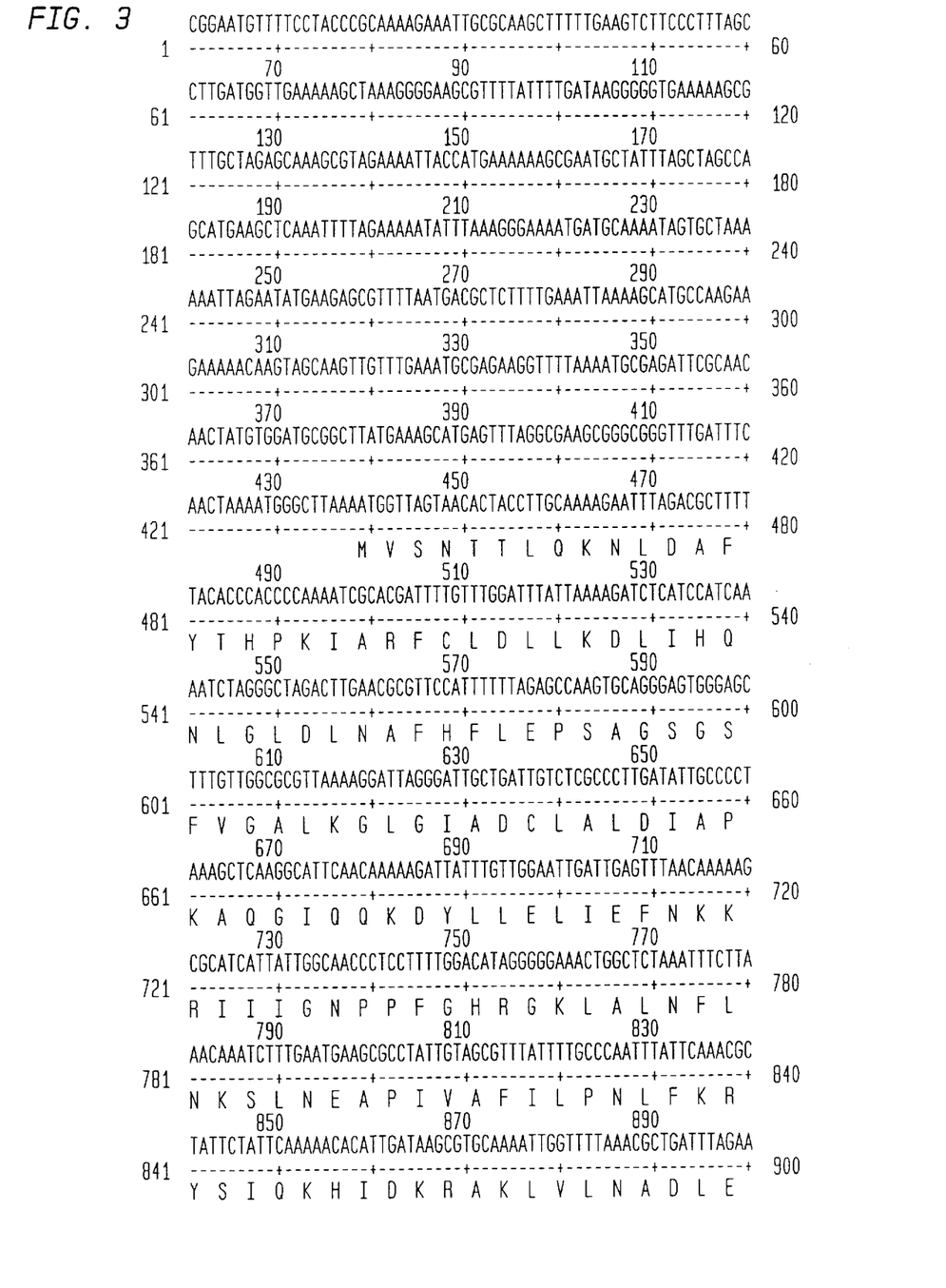
FIG. 3—Partial HpyCH4V methyltransferase amino acid sequence and DNA sequence at the HpyCH4V gene locus (SEQ ID NO:3, SEQ ID NO:4).

1. DNA Sequencing: DNA sequencing was performed on double-stranded templates on an ABI 373 automated sequencer. Individual clones were sequenced from primers located in the vector on both sides of the inserts. The DNA sequencing of the clones was incomplete at time of filing. Computer analyses of the DNA sequences obtained were performed with the Genetics Computer Group programs (Deverenx, et al., *Nucleic Acids Res.* 12:387–395 (1984)) and database similarity searches were performed via the internet at the National Center for Biotechnology Information site (http://www.ncbi.nlm.nih.gov/BLAST/) using the BLASTX algorithm (Altschul, et al., *J. Mol. Biol* 215:403–410 (1990) and Gish, et al., *Nature Genet.* 3:266–722 (1993).). An open reading frame (ORF) of 462 bp which contained motifs 1 and 4 characteristic of gamma type N6-methyl adenine DNA methyltransferases was identified in DNA sequence reading from the vector into one end of the insert (SEQ ID NO:3 and SEQ ID NO:4, FIG. 3). This partial open reading frame was identified as the N-terminal portion of the HpyCH4V methyltransferase, designated HpyCH4VM. DNA 5' to the HpyCH4V methyltransferase matches with genes JHP1440 and JHP1441 in the sequenced genome of strain J99, with the ATG start of the HpyCH4V methyltransferase gene located 13 bp 3' to the stop codon of the JHP1441 gene. The sequence of the HpyCH4V methyltransferase clone diverges from the J99 strain immediately following the stop codon of the JHP1441 gene, and the sequence of the HpyCH4V methyltransferase gene is not present in strain J99, nor in the other sequenced *Helicobacter pylori* strain, 26695. This is consistent with the observation that the genomic DNA of both strains J99 and 26695 is cleaved with the HpyCH4V endonuclease of the present invention. DNA sequence from the other end of the HpyCH4V methyl-transferase clones matches sequence in ORFs JHP1444 or JHP1445 of strain J99, and thus is presumed to be located beyond the HpyCH4V methylase and endonuclease genes.

A sample of an *E. coli* containing pHpyCH4VA3 (NEB#1240) has been deposited under the terms and conditions of the Budapest Treaty with the American Type Culture Collection on Sep. 23, 1999, and received ATCC Patent Accession No. PTA-782.

What is claimed is:

1. Isolated DNA coding for the HpyCH4V restriction endonuclease, wherein the isolated DNA is obtainable from *Helicobacter pylori*.

2. A recombinant DNA vector comprising a vector into which a DNA segment coding for the HpyCH4V restriction endonuclease has been inserted.

3. Isolated DNA coding for the HpyCH4V restriction endonuclease and methylase, wherein the isolated DNA is obtainable from ATCC Patent Accession No. PTA-782.

4. A cloning vector which comprises the isolated DNA of claim 3.

5. A host cell transformed by the vector of claim 2 or 4.

6. A method of producing an HpyCH4V restriction endonuclease comprising culturing a host cell transformed with the vector of claim 2 or 4 under conditions suitable for expression of said endonuclease.

7. A substantially pure Type II restriction endonuclease obtainable from *Helicobacter pylori* (ATCC Patent Accession No. PTA-781) recognizing the following base sequence in double-stranded deoxyribonucleic acid molecules:

$$5'\text{-TG}\downarrow\text{CA-}3'$$

$$3'\text{-AC}_\uparrow\text{GT-}5'$$

and having a cleavage position defined by the arrows.

8. A method for obtaining the Type II restriction endonuclease of claim 7, comprising cultivating a sample of *Helicobacter pylori* under conditions favoring the production of said endonuclease and separating said endonuclease therefrom.

9. The Type II restriction endonuclease of claim 7, wherein the restriction endonuclease is purified from *Helicobacter pylori* (ATCC Patent Accession No. PTA-781).

* * * * *

UNITED STATES PATENT AND TRADEMARK OFFICE
CERTIFICATE OF CORRECTION

PATENT NO. : 6,133,009

DATED: October 17, 2000

INVENTOR(S): Richar D. Morgan and Qing Xu

It is certified that errors appear in the above-identified patent and that said Letters Patent is hereby corrected as shown below:

| | |
|---|---|
| In the Title | before "Type II" insert --A Novel-- |
| In the Abstract | replace "3'-AC₀GT-5'" with --3'-AC↑GT-5'-- |
| Column 2, line 50 | replace "3'-AC₀GT-5'" with --3'-AC↑GT-5'-- |
| Column 3, line 5 | replace "aseparating" with --separating-- |
| Column 3, line 26 | replace "DNAS" with --DNAs-- |
| Column 3, line 62 | replace "3'-AC₀GT-5'" with --3'-AC↑GT-5'-- |
| Column 6, line 13 | replace "DATP" with --dATP-- |
| Column 12, line 4 | after "*pylori*" insert --CH4-- |
| Column 14, line 6 | replace "3'-AC₀GT-5'" with --3'-AC↑GT-5'-- |

Signed and Sealed this

Eighth Day of May, 2001

Attest:

NICHOLAS P. GODICI

Attesting Officer    Acting Director of the United States Patent and Trademark Office

UNITED STATES PATENT AND TRADEMARK OFFICE
CERTIFICATE OF CORRECTION

PATENT NO.   : 6,133,009
DATED        : October 17, 2000
INVENTOR(S)  : Morgan et al.

It is certified that error appears in the above-identified patent and that said Letters Patent is hereby corrected as shown below:

<u>Column 1,</u>
Line 6, insert -- This invention was made with Government support under contract number DK53707 awarded by the National Institutes of Health. The Government has certain rights in the invention. --

Signed and Sealed this

Twenty-eighth Day of January, 2003

JAMES E. ROGAN
*Director of the United States Patent and Trademark Office*

SEQUENCE LISTING

<160> NUMBER OF SEQ ID NOS: 5

<210> SEQ ID NO 1
<211> LENGTH: 6
<212> TYPE: DNA
<213> ORGANISM: Haemophilus aegyptius

<400> SEQUENCE: 1 wggccw                                                                      6

<210> SEQ ID NO 2
<211> LENGTH: 6
<212> TYPE: DNA
<213> ORGANISM: Escherichia coli

<400> SEQUENCE: 2 gaattc                                                                      6

<210> SEQ ID NO 3
<211> LENGTH: 900
<212> TYPE: DNA
<213> ORGANISM: Helicobacter pylori
<220> FEATURE:
<221> NAME/KEY: CDS
<222> LOCATION: (439)..(900)

<400> SEQUENCE: 3
cggaatgttt tcctacccgc aaaagaaatt gcgcaagctt tttgaagtct tccctttagc       60
cttgatggtt gaaaaagcta aagggaagc gttttatttt gataagggg tgaaaaagcg        120 tttgctagag caaagcgtag aaaattacca tgaaaaaagc gaatgctatt tagctagcca      180
gcatgaagct caaattttag aaaaatattt aaagggaaaa tgatgcaaaa tagtgctaaa      240
aaattagaat atgaagagcg ttttaatgac gctctttttga aattaaaagc atgccaagaa    300 gaaaacaag tagcaagttg tttgaaatgc gagaaggttt taaaatgcga gattcgcaac      360
aactatgtgg atgcggctta tgaaagcatg agtttaggcg aagcgggcgg gtttgatttc     420
aactaaaatg gcttaaa atg gtt agt aac act acc ttg caa aag aat tta         471
                    Met Val Ser Asn Thr Thr Leu Gln Lys Asn Leu
                     1               5                   10 gac gct ttt tac acc cac ccc aaa atc gca cga ttt tgt ttg gat tta        519
Asp Ala Phe Tyr Thr His Pro Lys Ile Ala Arg Phe Cys Leu Asp Leu
            15                  20                  25 tta aaa gat ctc atc cat caa aat cta ggg cta gac ttg aac gcg ttc        567
Leu Lys Asp Leu Ile His Gln Asn Leu Gly Leu Asp Leu Asn Ala Phe
        30                  35                  40 cat ttt tta gag cca agt gca ggg agt ggg agc ttt gtt ggc gcg tta        615
His Phe Leu Glu Pro Ser Ala Gly Ser Gly Ser Phe Val Gly Ala Leu
    45                  50                  55

```
aaa gga tta ggg att gct gat tgt ctc gcc ctt gat att gcc cct aaa      663
Lys Gly Leu Gly Ile Ala Asp Cys Leu Ala Leu Asp Ile Ala Pro Lys
 60              65                  70                  75 gct caa ggc att caa caa aaa gat tat ttg ttg gaa ttg att gag ttt      711
Ala Gln Gly Ile Gln Gln Lys Asp Tyr Leu Leu Glu Leu Ile Glu Phe
                 80                  85                  90 aac aaa aag cgc atc att att ggc aac cct cct ttt gga cat agg ggg      759
Asn Lys Lys Arg Ile Ile Ile Gly Asn Pro Pro Phe Gly His Arg Gly
             95                 100                 105 aaa ctg gct cta aat ttc tta aac aaa tct ttg aat gaa gcg cct att      807
Lys Leu Ala Leu Asn Phe Leu Asn Lys Ser Leu Asn Glu Ala Pro Ile
         110                 115                 120 gta gcg ttt att ttg ccc aat tta ttc aaa cgc tat tct att caa aaa      855
Val Ala Phe Ile Leu Pro Asn Leu Phe Lys Arg Tyr Ser Ile Gln Lys
     125                 130                 135 cac att gat aag cgt gca aaa ttg gtt tta aac gct gat tta gaa          900
His Ile Asp Lys Arg Ala Lys Leu Val Leu Asn Ala Asp Leu Glu
140                 145                 150
```

<210> SEQ ID NO 4
<211> LENGTH: 154
<212> TYPE: PRT
<213> ORGANISM: Helicobacter pylori

<400> SEQUENCE: 4

```
Met Val Ser Asn Thr Thr Leu Gln Lys Asn Leu Asp Ala Phe Tyr Thr
 1               5                  10                  15

His Pro Lys Ile Ala Arg Phe Cys Leu Asp Leu Leu Lys Asp Leu Ile
             20                  25                  30

His Gln Asn Leu Gly Leu Asp Leu Asn Ala Phe His Phe Leu Glu Pro
         35                  40                  45

Ser Ala Gly Ser Gly Ser Phe Val Gly Ala Leu Lys Gly Leu Gly Ile
     50                  55                  60

Ala Asp Cys Leu Ala Leu Asp Ile Ala Pro Lys Ala Gln Gly Ile Gln
 65                  70                  75                  80

Gln Lys Asp Tyr Leu Leu Glu Leu Ile Glu Phe Asn Lys Lys Arg Ile
                 85                  90                  95

Ile Ile Gly Asn Pro Pro Phe Gly His Arg Gly Lys Leu Ala Leu Asn
            100                 105                 110

Phe Leu Asn Lys Ser Leu Asn Glu Ala Pro Ile Val Ala Phe Ile Leu
        115                 120                 125

Pro Asn Leu Phe Lys Arg Tyr Ser Ile Gln Lys His Ile Asp Lys Arg
    130                 135                 140

Ala Lys Leu Val Leu Asn Ala Asp Leu Glu
145                 150
```

<210> SEQ ID NO 5
<211> LENGTH: 17
<212> TYPE: DNA
<213> ORGANISM: Helicobacter pylori

<400> SEQUENCE: 5
gttttcccag tcacgac      17